(12) United States Patent
Hicks et al.

(10) Patent No.: US 10,695,497 B2
(45) Date of Patent: Jun. 30, 2020

(54) SUBCUTANEOUS JET INJECTOR WITH A MANUALLY OPERATED INJECTOR PUMP

(71) Applicant: International Business Machines Corporation, Armonk, NY (US)

(72) Inventors: Andrew C. Hicks, Poughkeepsie, NY (US); Alex M. Hytha, Phoenixville, PA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 281 days.

(21) Appl. No.: 15/665,724

(22) Filed: Aug. 1, 2017

(65) Prior Publication Data

US 2019/0038838 A1    Feb. 7, 2019

(51) Int. Cl.
  *A61M 5/30*    (2006.01)
  *A61M 5/20*    (2006.01)

(52) U.S. Cl.
  CPC .............. *A61M 5/30* (2013.01); *A61M 5/2053* (2013.01); *A61M 2005/202* (2013.01)

(58) Field of Classification Search
  CPC .............................. A61M 5/30; A61M 5/2053
  See application file for complete search history.

(56) References Cited

U.S. PATENT DOCUMENTS

| | | | |
|---|---|---|---|
| 3,805,783 A | 4/1974 | Lsmach | |
| 4,059,107 A * | 11/1977 | Iriguchi | A61M 5/30 604/71 |
| 5,348,198 A | 9/1994 | Mizzi | |
| 5,984,140 A | 11/1999 | Amron | |
| 6,258,062 B1 | 7/2001 | Thielen | |
| 8,123,718 B2 | 2/2012 | Toles | |
| 8,684,968 B2 | 4/2014 | Genosar | |
| 2005/0180806 A1 * | 8/2005 | Green | A61B 17/8822 401/119 |
| 2016/0199579 A1 | 7/2016 | Boyd | |

FOREIGN PATENT DOCUMENTS

WO        9404437 A1        3/1994

OTHER PUBLICATIONS

List of IBM Patents or Patent Applications Treated as Related; (Appendix P), filed Nov. 10, 2017, 2 pages.
Andrew C. Hicks, et al., "Subcutaneous Jet Injector With a Manually Oeprated Injector Pump", Related Application, U.S. Appl. No. 115/805,646, filed Nov. 7, 2017, 16 pages.

* cited by examiner

*Primary Examiner* — Emily L Schmidt
(74) *Attorney, Agent, or Firm* — Cantor Colburn LLP; Teddi Maranzano

(57) ABSTRACT

A manual subcutaneous jet injector includes an injector body having an injection portion provided with an injection system including an injection fluid volume fluidically connected to a subcutaneous injector outlet, and a pumping portion. The pumping portion includes an interior chamber having a pumping portion and a pressure chamber portion fluidically connected to the injection fluid volume. A manually operated injector pump is arranged in the pumping portion. At least one one-way valve is arranged between the pumping portion and the pressure chamber portion, the one-way valve including an inlet end and an outlet end. A piston is arranged in the pumping portion at the inlet end of the one-way valve.

5 Claims, 3 Drawing Sheets

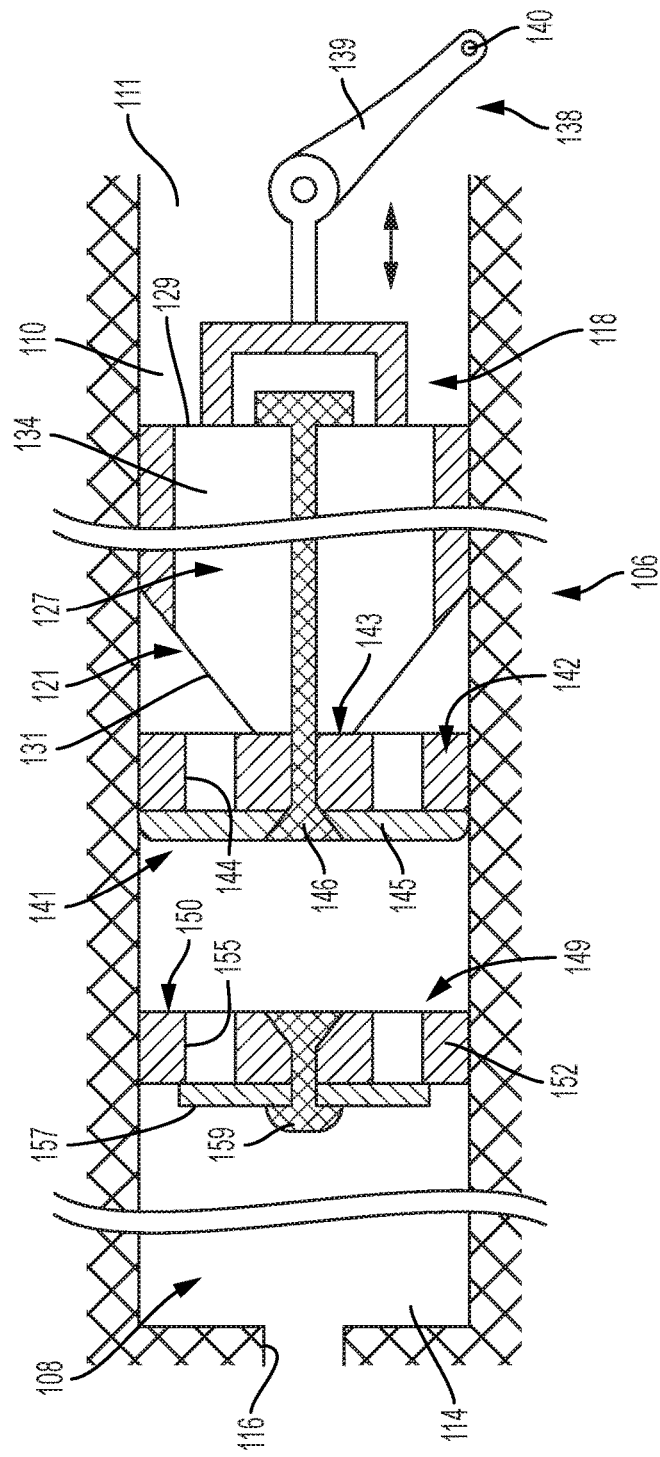
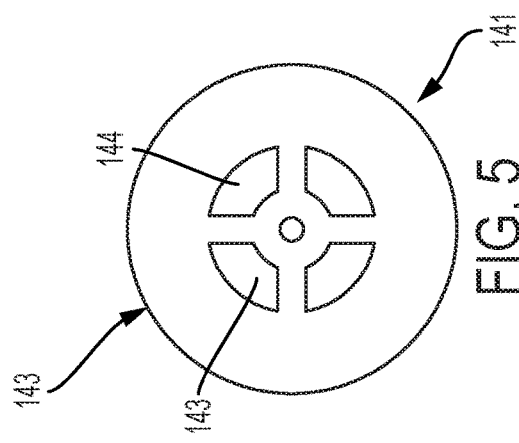
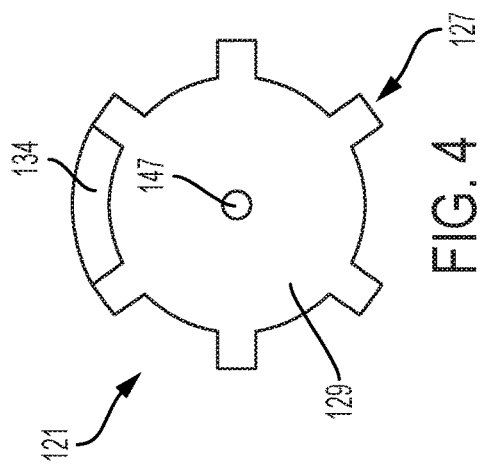

SUBCUTANEOUS JET INJECTOR WITH A MANUALLY OPERATED INJECTOR PUMP

BACKGROUND

The present invention relates to subdural injectors, and more specifically, to a subcutaneous jet injector with a manually operated injector pump.

There exist a variety of systems for subcutaneous introduction of a liquid into a body. Typically, a syringe including a hypodermic needle, a barrel, and a plunger is employed by medical personnel to introduce a liquid, such as a medicine, into a body. The needle may be introduced through an epidermal layer into the body. The plunger may then be depressed into the barrel. The plunger urges liquid from the barrel through the hypodermic needle into tissue between the epidermal layer and underlying muscle.

A jet injector represents another system for subcutaneous introduction of a liquid. A jet injector relies on a narrow jet of injection liquid that penetrates the epidermal layer. A pressurized gas, such as air or $CO_2$ forces the liquid through the epidermal layer. Essentially, the liquid itself becomes they hypodermic needle. The jet injector is typically employed for mass or high-volume usage such as for administering medicines to large groups of people. The jet injector may be coupled to the pressurized gas through a hose or may include an internal source of gas such as a $CO_2$ cartridge.

Jet injectors possess a number of advantages over hypodermic needles. For example, a jet injector produces less medical waste that may require special handling. However, jet injectors also require the source of pressurized gas. The pressurized gas, in the form of canisters, cartridges or the like may be difficult to obtain and or transport to more remote portions of the globe.

SUMMARY

According to an exemplary embodiment, a manual subcutaneous jet injector includes an injector body having an injection portion provided with an injection system including an injection fluid volume fluidically connected to a subcutaneous injector outlet, and a pumping portion. The pumping portion includes an interior chamber having a pumping portion and a pressure chamber portion fluidically connected to the injection fluid volume. A manually operated injector pump is arranged in the pumping portion. At least one one-way valve is arranged between the pumping portion and the pressure chamber portion, the one-way valve including an inlet end and an outlet end. A piston is arranged in the pumping portion at the inlet end of the one-way valve.

According to another aspect of an exemplary embodiment, a method of manually charging a subcutaneous jet injector includes shifting a piston arranged within a pressure chamber portion of the subcutaneous jet injector, forcing a fluid through a one-way valve with the piston into a chamber of the subcutaneous jet injector, pressurizing the fluid in the chamber creating a pressurized fluid, forcing the pressurized fluid in the chamber into another chamber including a bolus dose of injectable fluid, and directing the bolus dose of injectable fluid from the subcutaneous jet injector with the pressurized fluid.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 3 depicts a subcutaneous jet injector having a manual injector pump, in accordance with yet another aspect of an exemplary embodiment;

FIG. 4 depicts an axial end view of a piston associated with the manual injector pump of FIG. 3, in accordance with an aspect of an exemplary embodiment; and FIG. 5 depicts an axial end view of a one-way valve associated with the manual injector pump of FIG. 3, in accordance with an aspect of an exemplary embodiment.

DETAILED DESCRIPTION

Figure 1:
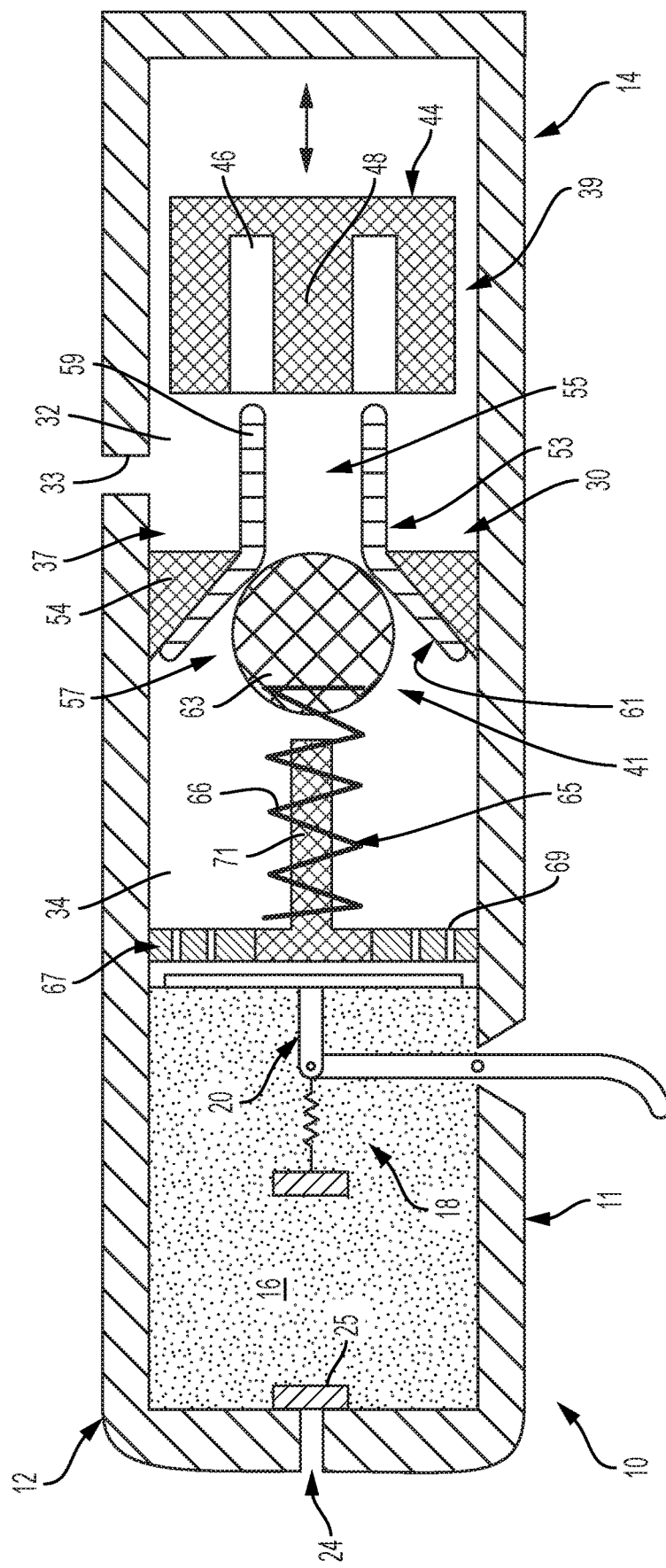
FIG. 1 depicts a subcutaneous jet injector having a manual injector pump, in accordance with an aspect of an exemplary embodiment.

A manual subcutaneous jet injector, in accordance with an exemplary embodiment, is illustrated generally at 10 in FIG. 1. Subcutaneous jet injector 10 includes an injector body 11 including an injection portion 12 that stores and delivers a bolus dose, and a pump portion 14 that generates a fluidic pressure that provides a motive force which aids in delivery of the bolus dose. Injection portion 12 includes an injection fluid volume 16 which may store the bolus does and an injection system 18 that triggers delivery of the bolus dose. Injection system 18 includes a pressure release system 20 that may facilitate delivery of a pressurized fluid from pump portion 14 into injection fluid volume 16. The bolus dose may then pass through a subcutaneous injector outlet 24 that may be provided with a valve 25.

In accordance with an exemplary embodiment, pump portion 14 includes an interior chamber 30 defining a pumping portion 32 having an inlet 33 and a pressure chamber portion 34. A manually operated injector pump 37 is arranged at pumping portion 32. Manually operated injector pump 37 includes a piston 39 and a one-way valve 41. Piston 39 includes a piston body 44 having an annular groove 46 that defines a compression member 48 which, as will be detailed herein, selectively extends into and out of one-way valve 41.

In further accordance with an exemplary embodiment, one-way valve 41 includes a valve seat 53 that may be formed from a compliant material. Valve seat 53 is supported by a wall member 54 that may take the form of a compliant section (not separately labeled) arranged between pumping portion 32 and pressure chamber portion 34. Valve seat 53 includes an inlet end 55 and an outlet end 57. Inlet end 55 is defined by a wall member 59 that is receptive to compression member 48 of piston 39. In operation, developed pressure may seal wall member 59 about compression member 48 during a portion of a stroke of piston 39.

Outlet end 57 includes a generally conical shape 61 that is receptive to a check ball 63. Thus, in the exemplary embodiment shown, one-way valve 41 defines a ball valve. A biasing element 65 such as a spring 66 urges check ball 63 into outlet end 57 sealing one-way valve 41. Biasing element 65 may be supported by a wall 67 having a plurality of openings, one of which is indicated at 69. In accordance with an exemplary aspect, biasing element 65 is supported by a post 71 arranged in wall 67.

Pressure developed by compression member 48 passing into inlet end 55 may unseat check ball 63 allowing an amount of fluid to enter into pressure chamber portion 34. Continued reciprocal movement of piston 39, developed by, for example, shaking subcutaneous jet injector 10, may cause a pressure of the fluid in pressure chamber portion 34 to rise. In accordance with an exemplary embodiment, manually operated pump 37 may develop a pressure of at least about 850 psi (5860.5 kPa) in pressure chamber portion 34.

Figure 2:
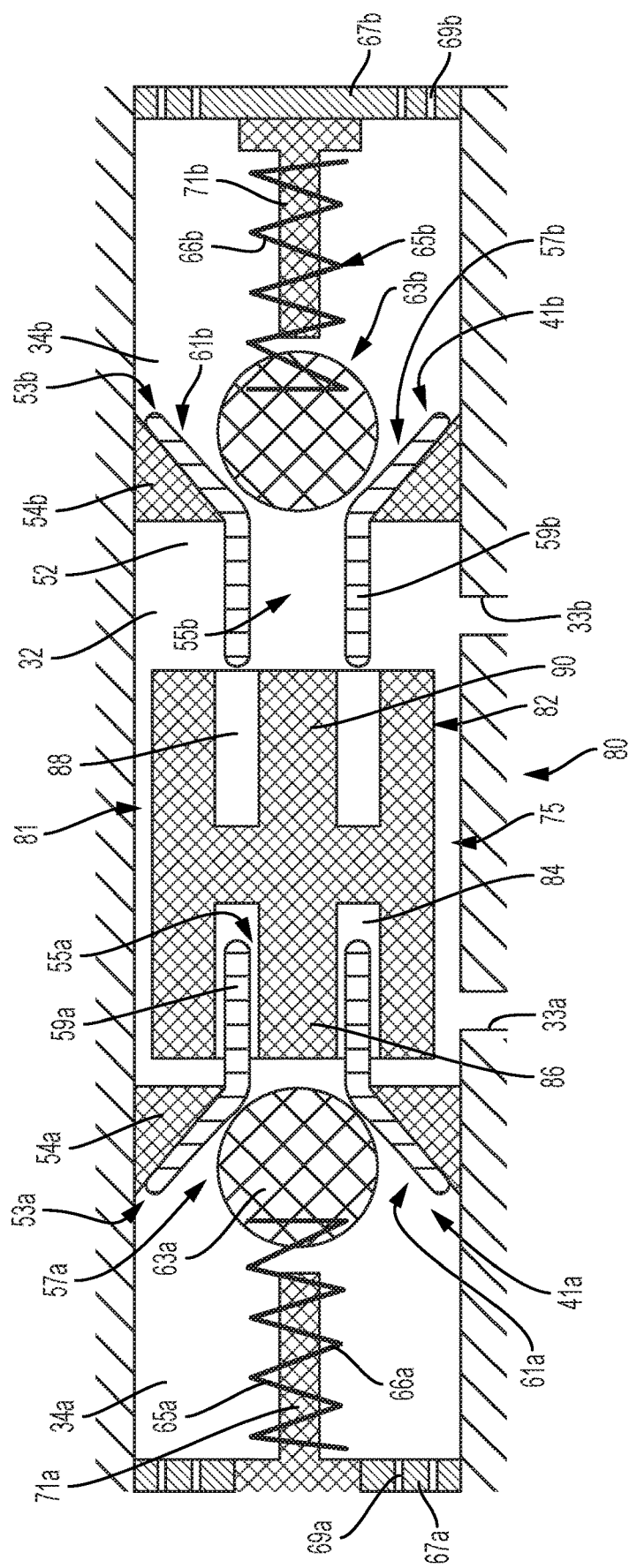
FIG. 2 depicts a subcutaneous jet injector having a manual injector pump, in accordance with another aspect of an exemplary embodiment.

Reference will now follow to FIG. 2, wherein like reference numerals define corresponding parts in the respective views in describing a pump portion 80 in accordance with another aspect of an exemplary embodiment. Pump portion 80 includes pumping portion 32 having a first and second inlets 33a and 33b and a pair of opposing pressure chamber portions 34a, 34b. Pump portion 80 also includes a first one-way valve 41a and a second one-way valve 41b. A manually operated injector pump 75 is arranged at pumping portion 32. Manually operated injector pump 75 includes a piston 81 including a piston body 82 having a first annular groove 84 that defines a first compression member 86 that selectively extends into first one-way valve 41a and a second annular groove 88 that defines a second compression member 90, as will be detailed herein, selectively extends into and out of one-way valve 41b.

In further accordance with an exemplary embodiment illustrated in FIG. 2, one-way valve 41a includes a valve seat 53a that may be formed from a compliant material. Valve seat 53a is supported by a wall member 54a which may define a compliant section (not separately labeled). Valve seat 53a includes an inlet end 55a and an outlet end 57a. Inlet end 55a is defined by a wall member 59a that may define another compliant section (also not separately labeled) which is receptive to first compression member 86 of piston 81. In operation, developed pressure may seal wall member 59a about first compression member 86 during a portion of a stroke of piston 81.

Outlet end 57a includes a generally conical shape 61a that is receptive to a check-ball 63a. Thus, in the exemplary embodiment shown, one-way valve 41a defines a ball valve. A biasing element 65a, such as a spring 66a urges check ball 63a into outlet end 57a sealing one-way valve 41a. Biasing element 65a may be supported by a wall 67a having a plurality of openings, one of which is indicated at 69a. In accordance with an exemplary aspect, biasing element 65a is supported by a post 71a arranged in wall 67a.

Similarly, second one-way valve 41b includes a valve seat 53b that may be formed from a compliant material. Valve seat 53b is supported by a wall member 54b. Valve seat 53b includes an inlet end 55b and an outlet end 57b. Inlet end 55b is defined by a wall member 59b that is receptive to second compression member 90 of piston 81. In operation, developed pressure may seal wall member 59b about second compression member 90 during a portion of a stroke of piston 81.

Outlet end 57b includes a generally conical shape 61b that is receptive to a check-ball 63b. Thus, in the exemplary embodiment shown, second one-way valve 41b defines a ball valve. A biasing element 65b, such as a spring 66b urges check ball 63b into outlet end 57b sealing second one-way valve 41b. Biasing element 65b may be supported by a wall 67b having a plurality of openings, one of which is indicated at 69b. In accordance with an exemplary aspect, biasing element 65b is supported by a post 71b arranged in wall 67b.

In operation, reciprocal motion of piston 81 causes first compression member 86 to move into and out of inlet end 55a unseating check ball 63a allowing an amount of fluid to pass into first pressure chamber portion 34a. Likewise, second compression member 90 moves into and out of inlet end 55b of second one-way valve 41b allowing an amount of fluid to pass into second pressure chamber portion 34. Continued reciprocal movement of piston 81, developed by, for example, shaking subcutaneous jet injector 10, may cause a pressure of the fluid in first and second pressure chamber portions 34a, 34b to rise. In accordance with an exemplary embodiment, manually operated injector pump 75 may develop a pressure of at least about 850 psi (5860.5 kPa) in first and second pressure chamber portions 34a, 34b.

Reference will now follow to FIGS. 3-5 in describing a pump portion 106 in accordance with another aspect of an exemplary embodiment. Pump portion 106 includes an interior chamber 108 defining a pumping portion 110 including an inlet 111 and a pressure chamber portion 114 having an outlet 116. A manually operated pump 118 may be arranged in pumping portion 110. Manually operated pump 118 includes a piston 121 having a piston body 127 defining an inlet end portion 129 and an outlet end portion 131. A plurality of channels, one of which is indicated at 134, extends between inlet end portion 129 and outlet end portion 131. Channels 134 define a recess (not separately labeled) formed in piston body 127 as shown in FIG. 4. A manual actuator 138 may be coupled to piston 121. Manual actuator 138 may include a lever 139 that may pivot about a point 140 driving piston 121 in a reciprocal motion within pumping portion 110.

In further accordance with an exemplary aspect, manually operated pump 118 includes a first one-way valve 141 mounted at outlet end portion 131 of piston 121. It is to be understood that the particular location of first one-way valve 141 may vary. For example, first one-way valve 141 may be configured to mount at inlet end portion 129 of piston 121. First one-way valve 141 defines a first poppet valve 142 including a first valve body 143 including a first plurality of passages, one of which is indicated at 144 as shown in FIG. 5. Passages 144 may be selectively covered by a first resilient, deformable, valve member 145. Valve member 145 may be secured to first poppet valve 142 through a first mechanical fastener 146 that may extend through a passage 147 (FIG. 5) passing through piston 121.

In still further accordance with an exemplary aspect, manually operated pump 118 includes a second one-way valve 149 positioned between first one-way valve 140 and pressure chamber portion 114. Second one-way valve 149 may define a second poppet valve 150 having a second valve body 152 including a second plurality of passages 155 that may be selectively covered by a second resilient, deformable, valve member 157 that may be secured to second valve body 152 through a second mechanical fastener 159.

In operation, piston 121 shifts within pumping portion 110. During a first stroke portion, induced through manipulation of manual actuator 138, wherein piston 121 is moving toward inlet 111, first valve member 145 deflect outwardly allowing fluid to pass into inlet end portion 129, flow through outlet end portion 131 and pass through first one-way valve 140. Further manipulation of manual actuator 138 drives piston 121 toward outlet 116 forcing the fluid through second one-way valve 149 into pressure chamber portion 114. In accordance with an exemplary embodiment, manually operated pump 118 may develop a pressure of at least about 850 psi (5860.5 kPa) in pressure chamber portions 114. Pressure accumulated in pressure chamber portion 114 may be used to force the bolus dose through subcutaneous injector outlet 24.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated While the preferred embodiment of the invention had been described, it will be understood that those skilled in the art, both now and in the future, may make various improvements and enhancements which fall within the scope of the claims which follow. These claims should be construed to maintain the proper protection for the invention first described.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

What is claimed is:

1. A manual subcutaneous jet injector comprising:
an injector body including an injection portion having an injection system including an injection fluid volume fluidically connected to a subcutaneous injector outlet comprising:
an interior chamber including a pumping portion and a pressure chamber portion fluidically connected to the injection fluid volume;
a manually operated injector pump arranged in the pumping portion, the manually operated injector pump comprising;
at least one one-way valve arranged between the pumping portion and the pressure chamber portion, the one-way valve including an inlet end and an outlet end; and
a piston arranged in the pumping portion at the inlet end of the one-way valve,
wherein the piston includes a compression member selectively extending into the inlet end of the at least one one-way valve.

2. The manual subcutaneous jet injector according to claim 1, wherein the at least one one-way valve comprises a ball valve including a check ball arranged at the outlet end.

3. The manual subcutaneous jet injector according to claim 2, wherein the at least one one-way valve includes a valve seat defining the inlet end and the outlet end, at least a portion of the valve seat being formed from a compliant material.

4. The manual subcutaneous jet injector according to claim 2, further comprising: a biasing element acting upon the check ball, the biasing element urging the check ball towards the inlet end.

5. The manual subcutaneous jet injector according to claim 1, wherein the piston includes an inlet end portion, an outlet end portion, and one or more channels extending between the inlet end portion and the outlet end portion.

* * * * *